(12) United States Patent
Dai et al.

(10) Patent No.: US 9,580,230 B2
(45) Date of Patent: Feb. 28, 2017

(54) ANTI-JAM DISPENSER

(71) Applicant: Honeywell International Inc., Morristown, NJ (US)

(72) Inventors: Tony Dai, Shanghai (CN); Mark Hua, Shanghai (CN); Jex Zhang, Shanghai (CN); Oliver Li, Shanghai (CN)

(73) Assignee: Honeywell International, Inc., Morris Plains, NJ (US)

( * ) Notice: Subject to any disclaimer, the term of this patent is extended or adjusted under 35 U.S.C. 154(b) by 0 days.

(21) Appl. No.: 14/504,017

(22) Filed: Oct. 1, 2014

(65) Prior Publication Data
US 2016/0096675 A1    Apr. 7, 2016

(51) Int. Cl.
| | |
|---|---|
| G07F 11/44 | (2006.01) |
| B65D 83/00 | (2006.01) |
| A61F 11/08 | (2006.01) |
| B65D 83/04 | (2006.01) |
| A45C 11/00 | (2006.01) |

(52) U.S. Cl.
CPC .......... B65D 83/0083 (2013.01); A61F 11/08 (2013.01); B65D 83/0409 (2013.01); G07F 11/44 (2013.01); *A45C 2011/007* (2013.01)

(58) Field of Classification Search
CPC .................................................... A61F 15/001
USPC .................................. 221/265, 186, 2, 25, 1
See application file for complete search history.

(56) References Cited

U.S. PATENT DOCUMENTS

| | | |
|---|---|---|
| 2,535,928 A | 12/1950 | Ives |
| 2,630,245 A | 3/1953 | Maier |
| 2,772,811 A | 12/1956 | Schaef |
| 2,904,230 A | 9/1959 | Worth |
| 3,261,503 A | 7/1966 | Cassidy |
| 3,730,387 A | 5/1973 | McConnell et al. |
| 3,741,162 A | 6/1973 | Lopez |
| 3,811,599 A | 5/1974 | O'Connor |
| 3,885,703 A | 5/1975 | Neavin |
| 4,662,538 A | 5/1987 | Goudy, Jr. et al. |
| 4,782,981 A | 11/1988 | Schuster |

(Continued)

FOREIGN PATENT DOCUMENTS

| | | |
|---|---|---|
| EP | 1074236 A2 | 7/2001 |
| WO | 9409456 A1 | 4/1994 |

OTHER PUBLICATIONS

EP15187495.5, Extended European Search Report, mailed Feb. 10, 2016, 7 pages.

*Primary Examiner* — Timothy Waggoner
*Assistant Examiner* — Ayodeji Ojofeitimi
(74) *Attorney, Agent, or Firm* — Conley Rose, P.C.; Kristin Jordan Harkins (57) ABSTRACT

Embodiments of the disclosure include earplug dispensers that may comprise a rotating cam assembly operable to dispense one or more earplug to a user when a knob is rotated by the user. In some embodiments, the cam assembly may comprise and upper cam layer and a lower cam layer attached via clips to the rotating knob. Upon rotation of the knob, the upper cam layer may cause the earplugs to fall through one or more cavities to the lower cam layer. The lower cam layer may comprise a pushing structure operable to move the earplugs, upon rotation of the knob, within the lower cam layer to fall down through an opening in the dispenser. In some embodiments, the earplugs may fall through an opening in the rotating knob.

20 Claims, 8 Drawing Sheets

(56) References Cited

U.S. PATENT DOCUMENTS

| | | | |
|---|---|---|---|
| 5,014,877 A | 5/1991 | Roos | |
| 5,280,845 A | 1/1994 | Leight | |
| 5,285,925 A | 2/1994 | Leight | |
| 5,316,517 A | 5/1994 | Chiba et al. | |
| 5,322,185 A | 6/1994 | Leight | |
| 5,372,278 A | 12/1994 | Leight | |
| 5,518,149 A | 5/1996 | Lotspeich et al. | |
| 5,695,395 A | 12/1997 | Ota et al. | |
| 5,954,229 A | 9/1999 | Scholey et al. | |
| D424,340 S | 5/2000 | Fleming | |
| 6,241,120 B1 * | 6/2001 | Scholey | A47F 1/10 221/186 |
| 6,283,339 B1 | 9/2001 | Morrow | |
| 6,299,019 B1 * | 10/2001 | Leight | A61F 15/001 221/186 |
| 6,604,653 B2 | 8/2003 | Millar | |
| 6,991,131 B2 | 1/2006 | Maser | |
| 7,992,748 B2 * | 8/2011 | Lawrence | A47F 1/10 221/203 |
| 2002/0043538 A1 | 4/2002 | Millar | |
| 2006/0006189 A1 | 1/2006 | Curtolo et al. | |
| 2008/0116219 A1 | 5/2008 | Lawrence | |
| 2010/0018987 A1 | 1/2010 | Hamer | |
| 2014/0054326 A1 | 2/2014 | Ophardt et al. | |
| 2014/0131378 A1 * | 5/2014 | Shih | A61J 7/04 221/211 |

\* cited by examiner

ANTI-JAM DISPENSER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Earplug dispensers may allow for one earplug, or a small number of earplugs, to be dispensed to a user at a time from a store of multiple earplugs. Dispensers provide a convenient way to deliver earplugs to a user, for example in a work environment where many different workers are required to wear earplugs on the job. Many dispensers rely on gravity to move earplugs through a dispensing mechanism.

SUMMARY

Aspects of the disclosure may include embodiments of an earplug dispenser comprising: a dispenser bottle operable to hold a plurality of earplugs; and a rotating cam assembly attached to the dispenser bottle, operable to dispense the earplugs from the dispenser bottle, the cam assembly comprising: an upper cam layer comprising at least one cavity operable to accept a single earplug; a lower cam layer attached to the upper cam layer, the lower cam layer comprising a pushing structure; and a rotating knob attached to the lower cam layer, operable to cause the lower cam layer to rotate when the rotating knob is manually rotated by a user, wherein upon rotation of the knob: the earplug may fall through the at least one cavity of the upper cam layer to the lower cam layer, and the earplug may be pushed by the pushing structure from the lower cam layer to an opening and may fall through the opening.

In some embodiments, the lower cam layer and rotating knob may rotate radially with respect to the dispenser bottle. In some embodiments, the dispenser may further comprise a cover operable to attach to the dispenser bottle and cover at least a portion of the rotating cam assembly. In some embodiments, the cover may comprise a lip located below the cavity in the upper cam layer, spaced sufficiently downward to allow an earplug to fit within the lower cam layer, and the earplug may be held within the lower cam layer by the lip until the pushing structure pushes the earplug to a center hole in the lip located about the rotating knob. In some embodiments, the upper cam layer may rigidly attach to the lower cam layer via clips, and the upper cam layer may be operable to rotate with the rotating knob and lower cam layer. In some embodiments, the upper cam layer may comprise a conical shape and a fin operable to move the earplugs in the dispenser bottle toward the at least one cavity, and the at least one cavity may comprise a plurality of cavities around the perimeter of the conical shape. In some embodiments, the lower cam layer may comprise a plurality of cavities operable to allow the earplug to fall into the lower cam layer, wherein the cavities of the lower cam layer align with the cavities of the upper cam layer. In some embodiments, the cam assembly may further comprise a lip operable to hold the earplug within the lower cam layer until the pushing structure pushes the earplug to a center hole in the lip about the rotating knob. In some embodiments, the pushing structure of the lower cam layer may comprise at least one angled wall on the interior of the lower cam layer operable to direct the earplug to fall through the rotating knob, and the angled wall may be oriented so that rotation of the lower cam layer will direct the earplug inward toward an opening in the rotating knob. In some embodiments, the at least one angled wall may comprise an angle of approximately 5 to 45 degrees with respect to the outer perimeter of the lower cam layer.

Additional aspects of the disclosure may include embodiments of an earplug dispenser comprising: a rotating cam assembly having an upper cam layer comprising at least one cavity operable to accept a single earplug; a lower cam layer attached to the upper cam layer, the lower cam layer comprising a pushing structure operable to direct the earplug through the lower cam layer; and a rotating knob attached to the lower cam layer, operable to cause the lower cam layer to rotate when the rotating knob is manually rotated by a user, wherein upon rotation of the knob: the earplug falls through the at least one cavity of the upper cam layer to the lower cam layer, and the earplug is pushed by the pushing structure to an opening for dispensing the earplug out of the dispenser.

In some embodiments, the pushing structure may further comprise at least one angled wall on the interior of the lower cam layer operable to direct the earplug to fall through a hole located toward the center of the lower cam layer. In some embodiments, the cam assembly of the earplug dispenser may further comprise a lip operable to hold the earplug within the lower cam layer until the pushing structure pushes the earplug to the hole. In some embodiments, the cam assembly may further comprise a cover operable to cover at least a portion of the rotating cam assembly, wherein the cover may comprise a lip located below the cavity in the upper cam layer, spaced sufficiently downward to allow an earplug to fit within the lower cam layer, and the earplug may be held within the lower cam layer by the lip until the pushing structure pushes the earplug to a hole in the lip. In some embodiments, the upper cam layer may rigidly attach to the lower cam layer via clips, and the upper cam layer may be operable to rotate with the rotating knob and lower cam layer.

Other aspects of the disclosure may include embodiments of an earplug dispenser comprising: a dispenser bottle operable to hold a plurality of earplugs; and a rotating cam assembly attached to the dispenser bottle, operable to dispense the earplugs, the cam assembly comprising: an upper cam layer comprising at least one cavity operable to accept an earplug; a lower cam layer attached to the upper cam layer, the lower cam layer comprising at least one cavity that aligns with the cavity of the upper cam layer, and a pushing structure operable to push the earplug through the lower cam layer, wherein the earplug falls through the cavities of the upper cam layer and the lower cam layer; a lip located below the cavity in the upper cam layer, spaced sufficiently downward to allow an earplug to fit within the lower cam layer, wherein the earplug is held within the lower cam layer by the lip until the pushing structure pushes the earplug to a hole in the lip; and a rotating knob attached to the lower cam layer, operable to cause the lower cam layer, and thereby the pushing structure, to rotate when the rotating knob is manually rotated by a user, wherein the earplug exits the cam assembly through the rotating knob.

In some embodiments, the pushing structure of the lower cam layer may comprise at least one angled wall on the interior of the lower cam layer operable to push the earplug to fall through the rotating knob when the pushing structure is rotated. In some embodiments, upon rotation of the lower cam layer, the angled wall of the pushing structure may push the earplug in a direction perpendicular to the surface of the angled wall, and the earplug may move axially along the angled wall from a position near the perimeter of the lower cam layer to a position near the center of the lower cam layer. In some embodiments, the at least one angled wall may comprise an angle of approximately 5 to 45 degrees with respect to the outer perimeter of the lower cam layer. In some embodiments, the upper cam layer may comprise a conical shape and a plurality of cavities around the perimeter of the conical shape, and the lower cam layer may comprise a plurality of cavities operable to allow the earplug to fall to the pushing structure of the lower cam layer, wherein the cavities of the lower cam layer may align with the cavities of the upper cam layer.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a nonexclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for dispensing earplugs from an earplug dispenser. And earplug dispenser may comprise a rotating cam assembly operable to dispense one or more earplug to a user when a knob is rotated by the user. In some embodiments, the cam assembly may comprise and upper cam layer and a lower cam layer attached via clips to the rotating knob. Upon rotation of the knob, the upper cam layer may cause the earplugs to fall through one or more cavities to the lower cam layer. The lower cam layer may comprise a pushing structure operable to move the earplugs, upon rotation of the knob, within the lower cam layer to fall down through an opening in the dispenser. In some embodiments, the pushing structure may comprise one or more angled walls operable to push an earplug from a position near the outer perimeter of the lower cam layer toward a position near the center of the lower cam layer, wherein the earplugs may fall through an opening located toward the center of the lower cam layer. In some embodiments, the earplugs may fall through an opening in the rotating knob.

Figure 1A:
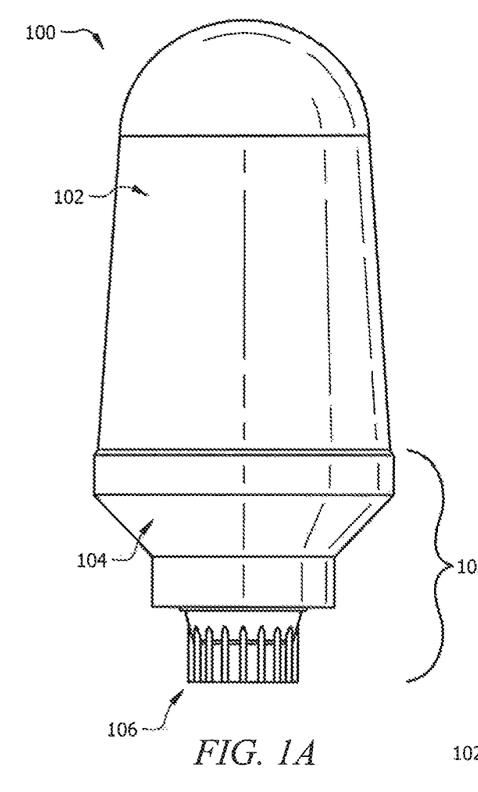
FIG. 1A illustrate an exemplary embodiment of an ear plug dispenser.
Figure 1B:
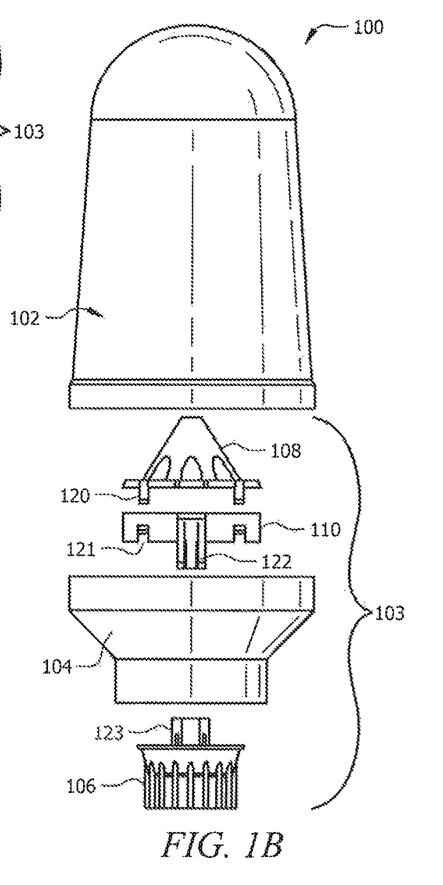
FIG. 1B illustrates an exploded view of the ear plug dispenser of FIG. 1A.

Referring now to FIGS. 1A-1B, an exemplary ear plug dispenser 100 is shown. The dispenser 100 may comprise a dispenser bottle 102, which may be operable to hold a plurality of earplugs. The dispenser bottle 102 may attach to a rotating cam assembly 103 operable to dispense earplugs from the dispenser bottle, wherein the rotating cam assembly 103 may comprise a cover 104, an upper cam layer 108, a lower cam layer 110, and a rotating knob 106. In the embodiment shown in FIGS. 1A-1B, the plurality of earplugs may be stored in the dispenser bottle 102, and the earplugs may move through the rotating cam assembly 103 via gravity, falling from the bottle 102 to the upper layer 108, the lower layer 110, and the rotating knob 106, wherein the earplugs may exit the dispenser 100 through an opening in the rotating knob 106. The upper cam layer 108 and the lower cam layer 110 may comprise cavities (not shown) for accepting the earplug(s) and allowing the earplug(s) to fall through the layers to the rotating knob 106. The rotation of the rotating knob 106, and therefore the lower layer 110 and upper layer 108, by a user may facilitate the movement of an earplug through the rotating cam assembly 103. Elements of the cam assembly 103 may rotate radially with respect to the dispenser bottle 102.

In some embodiments, the lower cam layer 110 may be rigidly attached to the rotating knob 106, such that when the knob 106 is manually rotated by a user, the lower cam layer 110 is also rotated. In some embodiments, the upper cam layer 108 may be rigidly attached to the lower cam layer 110, wherein the upper cam layer 108 may rotate with the lower cam layer 100. In some embodiments, the upper cam layer 108 may attach to the lower cam layer 110 via one or more clips 120, wherein the lower cam layer 110 may comprise one or more slots 121 for receiving the clips 120. In some embodiments, the lower cam layer 110 may attach to the rotating knob 106 via at least one clip 122, wherein the rotating knob 106 may comprise a slot 123 for receiving the clip 122.

In some embodiments, at least a portion of the cover 104 may fit between the lower cam layer 110 and the rotating knob 106 when assembled (as shown in FIG. 1A). In some embodiments, the cover 104 may attach to the dispenser bottle 102, for example via a screwing mechanism, a clipping mechanism, a snapping mechanism, or the like. In some embodiments, the cover 104 may cover the upper cam layer 108 and the lower cam layer 110, and possibly a portion of the rotating knob 106, when the earplug dispenser 100 is assembled (as shown in FIG. 1A).

Figure 2:
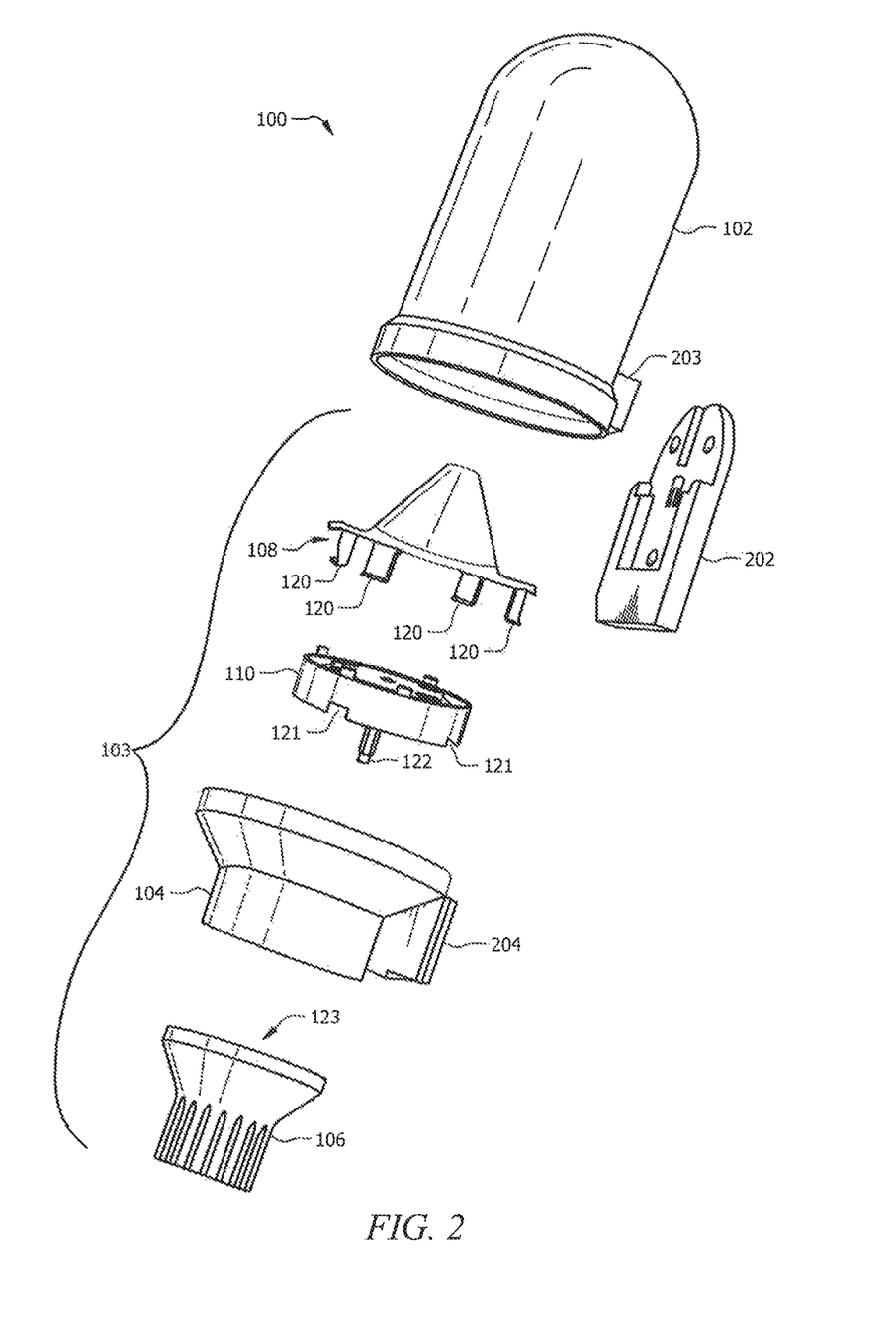
FIG. 2 illustrates a perspective, exploded view of an exemplary embodiment of an ear plug dispenser.

Referring now to FIG. 2, an exploded view of the earplug dispenser 100 is shown. In some embodiments, the earplug dispenser 100 may comprise an attachment interface 202 for attaching the dispenser 100 to a wall or other surface. In some embodiments, the dispenser bottle 102 and/or the cover 104 may comprise slots 203 and 204 for attaching the elements of the dispenser 100 to the attachment interface 202.

Figure 3:
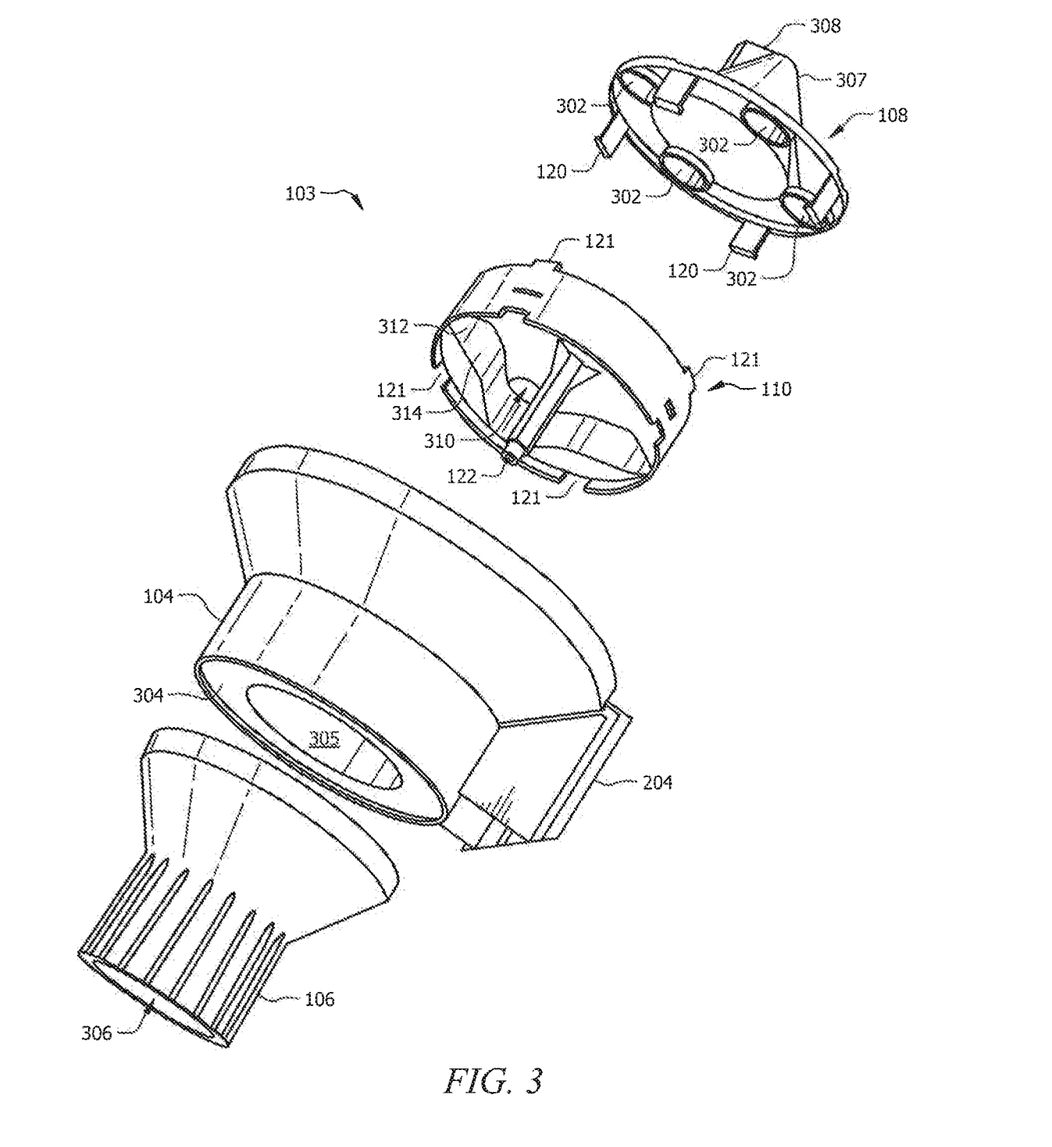
FIG. 3 illustrates a perspective, exploded view of an exemplary embodiment of a rotating cam assembly.

Referring now to FIG. 3, an exploded view of the rotating cam assembly 103 is shown. The upper cam layer 108 may comprise at least one cavity 302 (as described above) for allowing the earplug(s) to fall into the cam assembly 103. Additionally, in some embodiments, the upper cam layer 108 may comprise a conical shape 307 and a fin 308 operable to move the earplugs stored in the dispenser bottle 102 (not pictured) to the cavities 302 of the upper layer 108, wherein the cavities 302 are located around the perimeter of the conical shape 307. The lower cam layer 110 may comprise at least one cavity 310 (as described above) for allowing the earplug(s) to fall through the cam assembly 103, wherein the cavity 310 of the lower cam layer 110 may align with the cavity 302 of the upper cam layer 108. In some embodiments, the upper cam layer 108 and the lower cam layer 110 may comprise a plurality of cavities 302 and 310, wherein each cavity 302 of the upper layer 108 aligns with a cavity 310 of the lower cam layer 110.

In some embodiments, the cam assembly 103 may comprise a lip 304, wherein in the embodiment of FIG. 3, the lip 304 may be a part of the cover 104. The lip 304 may be operable to hold an earplug within the lower cam layer 110, wherein the earplug may fall through the cavity 310 of the lower cam layer 110 and rest on the lip 304. Additionally, the lower cam layer 110 may comprise a pushing structure 312 on the interior of the lower cam layer 110, wherein the pushing structure may move an earplug to the edge of the lip 304 causing it to fall through a hole 305 in the center of the lip 304. In the embodiment shown, the pushing structure 312 may comprise at least one angled wall 314, wherein when the lower cam layer 110 is rotated (by rotation of the rotating knob 106) the angled wall may push the earplug from a position near the outer perimeter of the lower cam layer 110 to a position near the center of the lower cam layer 110, causing the earplug to fall through the hole 305 of the lip 304. In some embodiments, after falling through the hole 305 of the lip 304, the earplug may then fall through an opening 306 in the rotating knob 106 to the user. In other embodiments, the earplug may fall through another portion of the cam assembly 103 to the user.

In some embodiments, the angled wall(s) 314 of the pushing structure 312 and the lip 304 may be spaced apart sufficiently to allow an earplug to fit between them by being compressed. This may prevent jamming of the cam assembly 103 by allowing the earplug to still be moved within the cam assembly 103 even if it somehow is positioned in a way as to move below the angled wall 314 (and above the lip 304), as opposed to the intended movement of the earplug within the lower cam layer 110. For example, a gap of approximately 6 millimeters may exist between the bottom surface of the angle wall(s) 314 of the pushing structure 312 and the top surface of the lip 304.

Figure 4A:
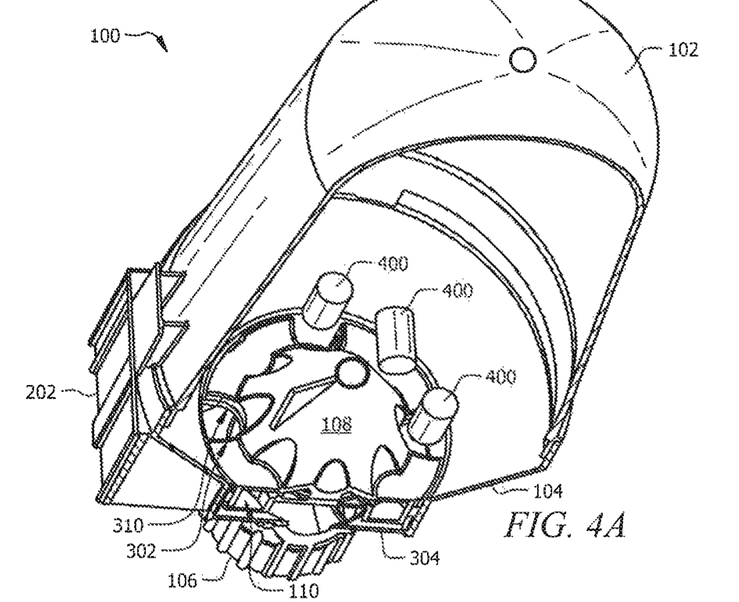
FIGS. 4A-4D illustrate a cut-away view of an exemplary embodiment of a rotating cam assembly used with an ear plug dispenser.
Figure 4B:
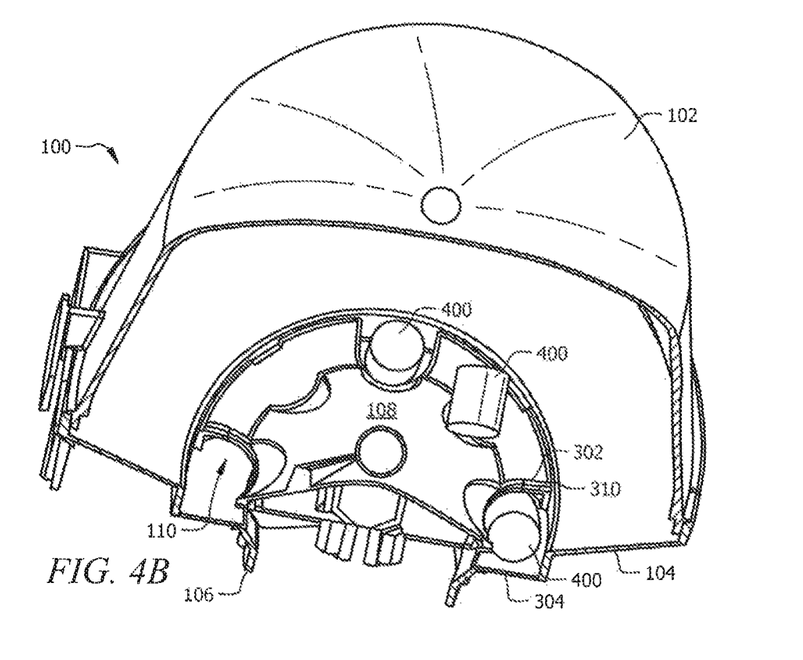
Figure 4C:
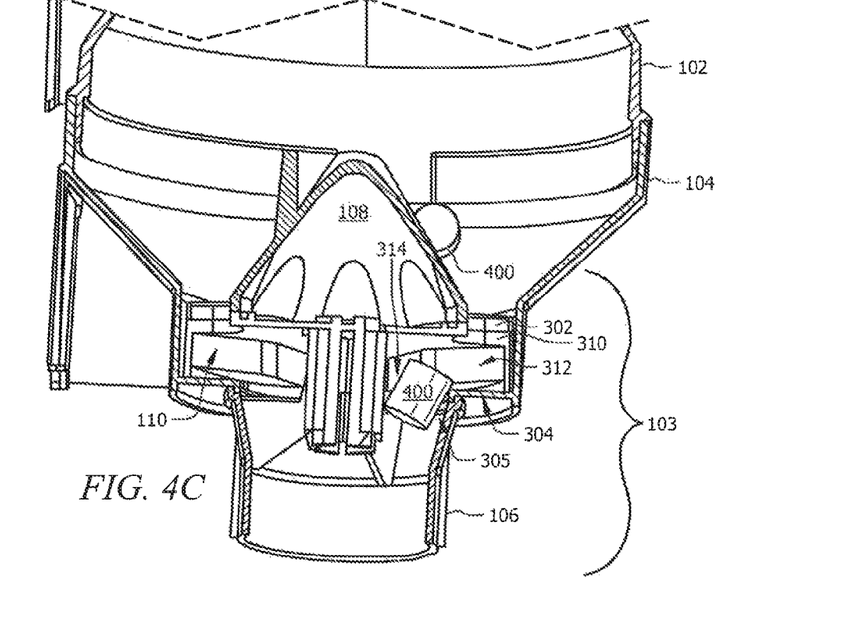
Figure 4D:
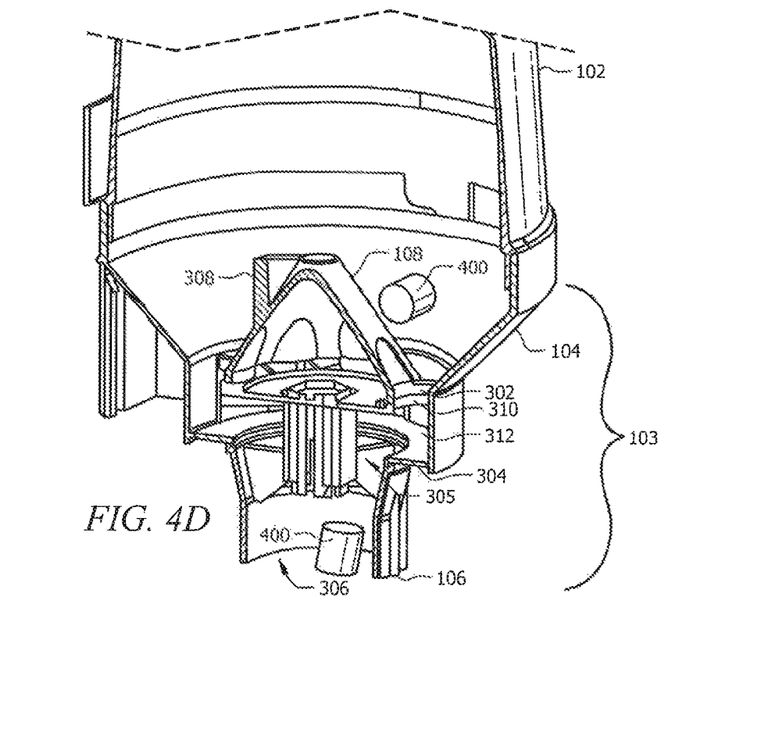

FIGS. 4A-4D illustrate detailed, cut-away views of an earplug 400 being dispensed from an earplug dispenser 100. In FIG. 4A, and earplug 400 may fall through the cavity 302 of the upper cam layer 108 and the cavity 310 of the lower cam layer 110. The cavities 302 and 310 may be designed to fit one earplug 400 at a time. In the embodiment shown, more than one earplug 400 may fall through more than one set of cavities 302 and 310. In FIG. 4B, the earplug 400 may rest on the lip 304 of the cover 104 and be held within the lower cam layer 110. As shown in FIG. 4C, upon rotation of the cam assembly 103, the earplug 400 may be pushed by the angled wall 314 of the pushing structure 312 off of the lip 304 and through the hole 305 into the rotating knob 106. As shown in FIG. 4D, the earplug 400 may then exit the cam assembly 103 through the opening 306 of the rotating knob 106. Additionally, it can be seen in FIG. 4C that a gap exists between the bottom surface of the pushing structure 312 and the top surface of the lip 304, allowing an earplug 400 to fit between the two surfaces if the earplug is jammed for some reason, thereby allowing the earplug 400 to still move within the cam assembly 103 when rotated.

In some embodiments, more than one earplug 400 may exit the dispenser 100 at a time, while in other embodiments, only one earplug 400 may exit the dispenser 100 at a time. The number of earplugs 400 that exit the dispenser 100 at a time may be determined by the number of cavities 302 and 310 in the upper cam layer 108 and lower cam layer 110. So, for example, in the embodiment shown in FIGS. 4A-4D, the upper cam layer 108 may comprise four cavities 302 and the lower cam layer 110 may comprise four cavities 310, thereby allowing up to four earplugs 400 to exit the cam assembly 103 at a time.

Figure 5A:
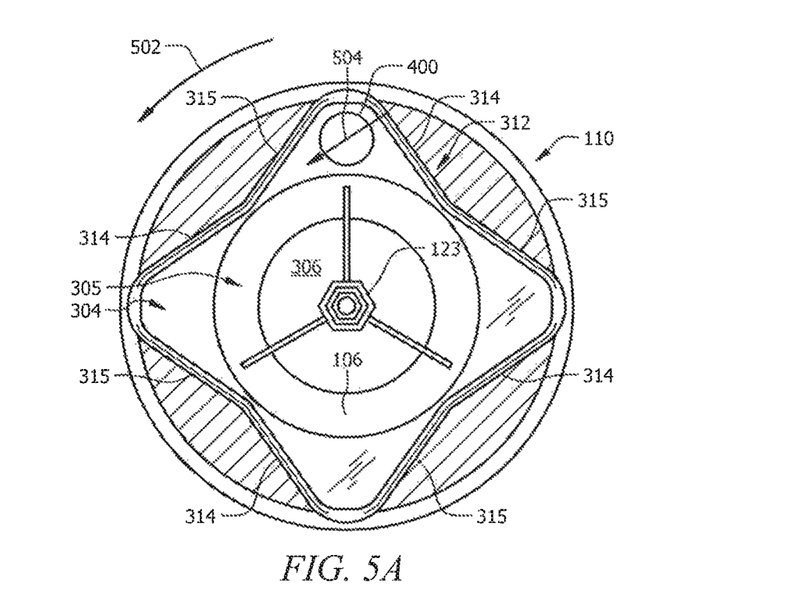
FIGS. 5A-5B illustrate a cut-away view of an exemplary embodiment of a pushing structure of a rotating cam assembly.
Figure 5B:
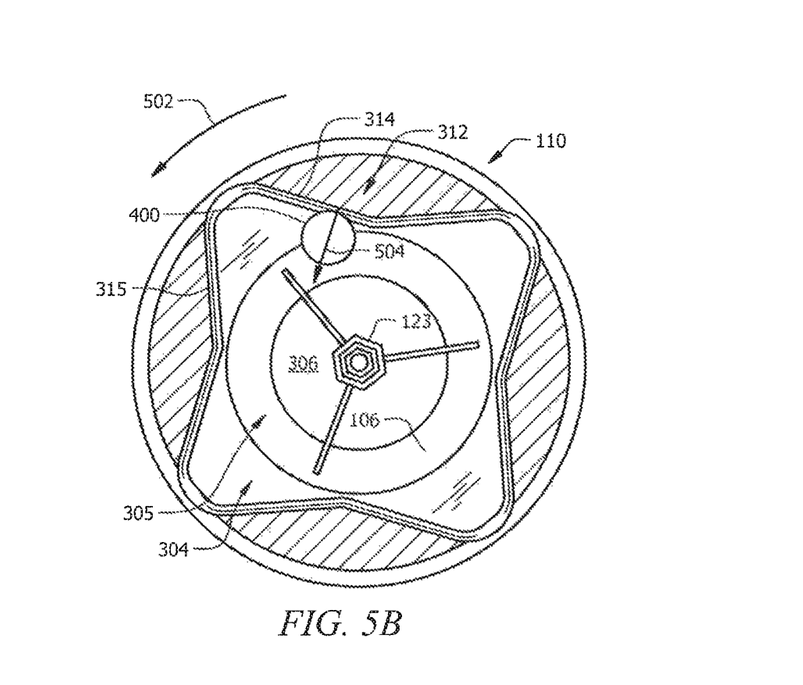

FIGS. 5A-5B illustrate a cut-away top view of the pushing structure 312 of the lower cam layer 110. In FIGS. 5A-5B, a top portion of the lower cam layer 110 has been cut away to show the pushing structure 312. As described above, an earplug 400 may fall through a cavity 310 (not pictured) of the lower cam layer 110 and be held within the lower cam layer 110 by the lip 304. The lower cam layer 110 and rotation knob 106 may rotate radially as shown by arrow 502. The angled wall 314 of the pushing structure 312 may contact the earplug 400, causing it to move perpendicularly to the angle of the angled wall 314, as shown by arrow 504. As the lower cam layer 110 rotates, the angled wall 314 will continue to push the earplug perpendicularly to the wall, wherein the earplug 400 may move along the angled wall toward the center of the lower cam layer 110. In other words, as the pushing structure 312 is rotated radially, the earplug 400 may be moved axially along the angled wall 314. In some embodiments, the angle of the angled wall 314 may be approximately 5 to 45 degrees with respect to the outer perimeter of the lower cam layer 110. In some embodiments, the angle of the angled wall 314 may be less than approximately 45 degrees with respect to the outer perimeter of the lower cam layer 110. In some embodiments, the angle of the angled wall 314 may be more than approximately 5 degrees with respect to the outer perimeter of the lower cam layer 110.

As shown in FIG. 5B, as the lower cam layer 110 is rotated, the earplug 400 may be pushed toward the center of the lower cam layer 110 and the center hole 305 of the lip 304, wherein the earplug 400 may fall through the hole 305 of the lip 304 and through the opening 306 of the rotating knob (located below the lower cam layer 110 and the lip 304) and may exit the dispenser to a user. In some embodiments, the pushing structure 312 may comprise a second angled wall 315 opposite to the first angled wall 314. In some embodiments, the angled walls 314 and 315 may keep the earplug contained within the lower cam layer 110. Additionally, when the lower cam layer 110 comprises multiple cavities (not shown), the pushing structure may comprise multiple first angled walls 314 and second angled walls 315, wherein the walls 314 and 315 may separate the earplugs from each other within the lower cam layer 110. In some embodiments, the second angled wall 315 may perform a similar function to the first angled wall 314 if the rotating knob 106 is rotated in a direction opposite the arrow 502, wherein the rotating cam assembly 103 may be rotated in either direction to dispense earplugs 400. As shown in FIGS. 5A-5B, the slot 123 operable to receive the clip 122 of the lower cam layer 110 (not shown) may be centered in the knob 106 in such a way as to allow earplugs 400 to fall around the slot 123.

Figure 6A:
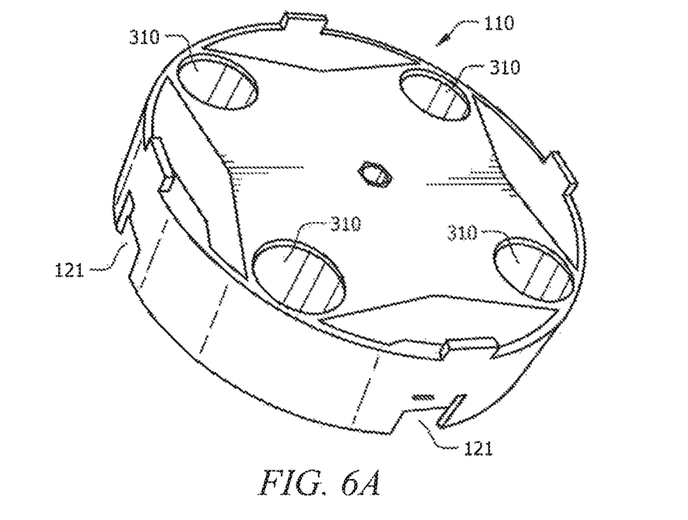
FIGS. 6A-6D illustrate detailed views of an exemplary embodiment of a lower cam layer of a rotating cam assembly.
Figure 6B:
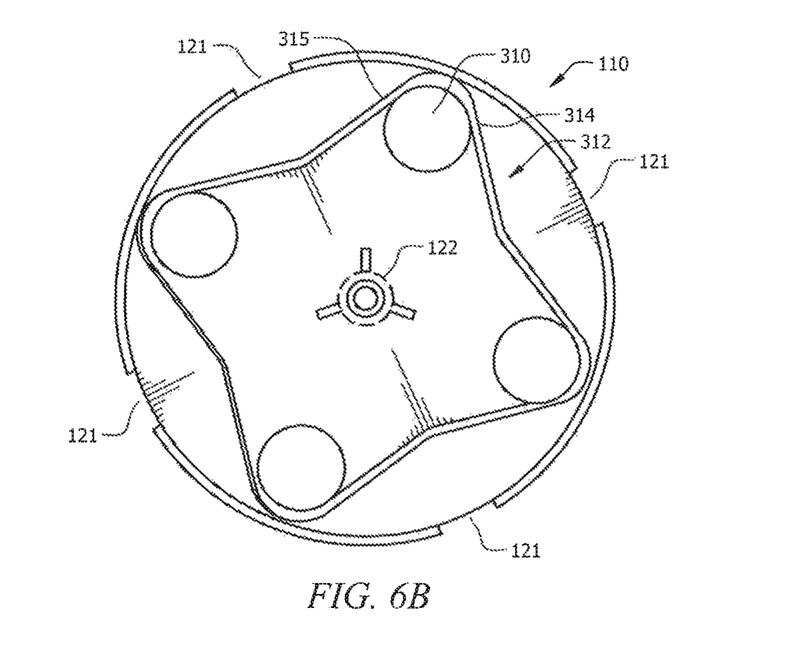
Figure 6C:
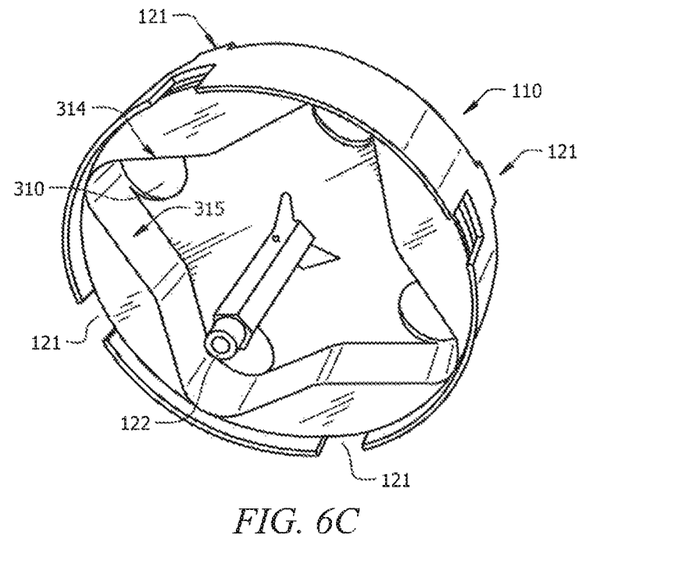
Figure 6D:
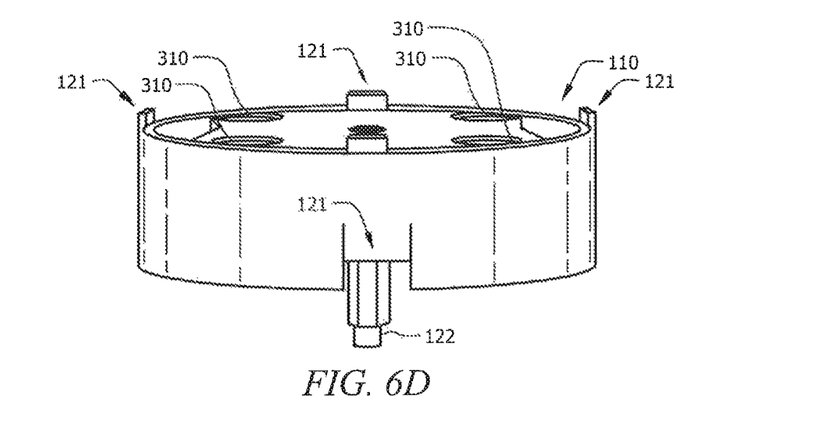

FIGS. 6A-6D illustrate detailed views of the lower cam layer 110 of the rotating cam assembly 103 (not pictured). The lower cam layer 110 comprises one or more cavities 310 and slots 121 for receiving clips (from the upper cam layer, not shown). The lower cam layer 110 also comprises the clip 122 for attaching to the rotating knob (not shown). The lower cam layer 110 also comprises the pushing structure 312, wherein the pushing structure 312 comprises one or more angled walls 314 and 315 for moving the earplugs within the pushing structure 312. In the embodiment of FIGS. 6A-6B, four cavities 310 are shown, but any number of cavities may be used to allow earplugs to fall into the lower cam layer 110. In the embodiment shown, each cavity 310 may be surrounded by a pair of angled walls 314 and 315 of the pushing structure 312.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of consisting essentially of and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An earplug dispenser comprising:
a dispenser bottle operable to hold a plurality of earplugs; and
a rotatable cam assembly attached to the dispenser bottle, operable to dispense the earplugs from the dispenser bottle, the rotatable cam assembly comprising:
an upper cam layer comprising one or more cavities, wherein each of the one or more cavities is configured to accept a single earplug from the dispenser bottle and pass the single earplug to a lower cam layer that is disposed below the upper cam layer;

the lower cam layer comprising a pushing structure; and a rotatable knob at least partially defining an opening that is disposed below the upper cam layer and the lower cam layer, wherein the rotatable knob is attached to the lower cam layer and the lower cam layer is attached to the upper cam layer such that rotation of the rotatable knob causes each of the lower cam layer and the upper cam layer to rotate, wherein the earplug dispenser is configured such that rotation of the rotatable knob over a first angular distance causes an earplug of the plurality of earplugs to fall through one of the one or more cavities of the upper cam layer to the lower cam layer, and wherein the earplug dispenser is further configured such that rotation of the rotatable knob over a second angular distance causes the pushing structure to displace the earplug that fell from the upper cam layer to the lower cam layer radially inward toward the center of the lower cam layer and toward the opening through which the earplug can fall.

2. The dispenser of claim 1, wherein the upper cam layer, the lower cam layer, and the rotatable knob are configured to rotate with respect to the dispenser bottle.

3. The dispenser of claim 1, further comprising a cover, wherein the cover is configured to retain at least a portion of the rotatable cam assembly with respect to the dispenser bottle.

4. The dispenser of claim 3, wherein the cover comprises a lip located below the one or more cavities in the upper cam layer, wherein the lip is spaced sufficiently downward to allow one or more of the plurality of earplugs to fit within the lower cam layer, and wherein the lip is configured to hold the earplug within the lower cam layer until the pushing structure is caused to displace the earplug radially inward.

5. The dispenser of claim 1, wherein the upper cam layer is rigidly attached to the lower cam layer via clips.

6. The dispenser of claim 1, wherein the upper cam layer comprises a conical shape and a fin, wherein the fin is operable to move at least one of the plurality of earplugs within the dispenser bottle toward the at least one of the one or more cavities, and wherein the upper cam layer comprises a plurality of cavities around the perimeter of the conical shape.

7. The dispenser of claim 1, wherein the lower cam layer comprises a plurality of cavities operable to allow the earplug to fall into the lower cam layer, and wherein each of the cavities of the lower cam layer is aligned with one of the one or more cavities of the upper cam layer.

8. The dispenser of claim 7, further comprising a cover comprising a lip located below the one or more cavities in the lower cam layer, wherein the lip is configured to operable to hold the earplug within the lower cam layer until the pushing structure is caused to displace the earplug radially inward.

9. The dispenser of claim 1, wherein the pushing structure of the lower cam layer comprises at least one angled wall on the interior of the lower cam layer, wherein the angled wall is operable to displace the earplug radially inward so as to fall through the opening.

10. The dispenser of claim 9, wherein the at least one angled wall comprises an angle of approximately 5 to 45 degrees with respect to an outer perimeter of the lower cam layer.

11. An earplug dispenser comprising:
a rotatable cam assembly having:
an upper cam layer comprising one or more cavities, wherein each of the one or more cavities is configured to accept one of the plurality of earplugs;

a lower cam layer comprising a pushing structure, wherein the pushing structure is configured to displace the earplug radially inward toward an opening; and a rotatable knob at least partially defining the opening that is disposed below the upper cam layer and the lower cam layer, wherein the rotatable knob is attached to the lower cam layer and the lower cam layer is attached to the upper cam layer such that rotation of the rotatable knob causes each of the lower cam layer and the upper cam layer to rotate, wherein the earplug dispenser is configured such that rotation of the rotatable knob over a first angular distance causes an earplug of the plurality of earplugs to fall through one of the one or more cavities of the upper cam layer to the lower cam layer, and wherein the earplug dispenser is further configured such that rotation of the rotatable knob over a second angular distance causes the pushing structure to displace the earplug that fell from the upper cam layer to the lower cam layer radially inward toward the center of the lower cam layer and toward the opening through which the earplug can fall.

12. The earplug dispenser of claim 11, wherein the pushing structure of the lower cam layer comprises at least one angled wall on the interior of the lower cam layer, wherein the angled wall is operable to displace the earplug radially inward so as to fall through the opening.

13. The earplug dispenser of claim 12 further comprising a lip operable to hold the earplug within the lower cam layer until the pushing structure is caused to displace the earplug radially inward.

14. The earplug dispenser of claim 11 further comprising a cover comprising a lip located below the one or more cavities in the upper cam layer, spaced sufficiently downward to allow one or more of the plurality of earplugs to fit within the lower cam layer, and wherein the lip is configured to hold the earplug within the lower cam layer until the pushing structure is caused to displace the earplug radially inward.

15. The earplug dispenser of claim 11, wherein the upper cam layer is rigidly attached to the lower cam layer via clips.

16. An earplug dispenser comprising:
a dispenser bottle operable to hold a plurality of earplugs; and a rotatable cam assembly attached to the dispenser bottle, operable to dispense the earplugs, the rotatable cam assembly comprising:
an upper cam layer comprising one or more cavities, wherein each of the one or more cavities is configured to accept an earplug, wherein the upper cam layer is configured such that an earplug is caused to fall through one of the one or more cavities of the upper layer to a lower cam layer upon rotation of the rotatable cam assembly over a first angular distance;

the lower cam layer comprising one or more cavities and a pushing structure, wherein each of the one or more cavities of the lower layer is aligned with one of the one or more cavities of the upper cam layer, and wherein, the pushing structure is configured to displace the earplug radially inward on a lip upon rotation of the rotatable cam assembly over a second angular distance;

the lip located below the one or more cavities in the upper cam layer, wherein the lip is spaced sufficiently downward to allow one or more of the plurality of earplugs to fit within the lower cam layer, wherein the lip is configured to hold the earplug within the lower cam layer until the pushing structure displaces the earplug radially inward toward the center of the lower cam layer and toward an opening that the earplug can fall through; and a rotatable knob at least partially defining the opening that is disposed below the lower cam layer, wherein the rotatable knob is attached to the lower cam layer and the lower cam layer is attached to the upper cam layer such that rotation of the rotatable knob causes each of the lower cam layer and the upper cam layer to rotate.

17. The dispenser of claim 16, wherein the pushing structure of the lower cam layer comprises at least one angled wall on the interior of the lower cam layer, wherein the angled wall is operable to displace the earplug radially inward so as to fall through the opening.

18. The dispenser of claim 17, wherein the lower cam layer is configured such that upon rotation of the lower cam layer, the angled wall of the pushing structure pushes the earplug in a direction perpendicular to the surface of the angled wall, and wherein the earplug moves axially along the angled wall from a position near an outer perimeter of the lower cam layer to a position near the center of the lower cam layer.

19. The dispenser of claim 17, wherein the at least one angled wall comprises an angle of approximately 5 to 45 degrees with respect to an outer perimeter of the lower cam layer.

20. The dispenser of claim 16, wherein the upper cam layer comprises a conical shape and a plurality of cavities around the perimeter of the conical shape, wherein the lower cam layer comprises a plurality of cavities, wherein each of the plurality of cavities of the lower layer is aligned with one of the cavities of the upper cam layer.

\* \* \* \* \*

UNITED STATES PATENT AND TRADEMARK OFFICE
CERTIFICATE OF CORRECTION

PATENT NO. : 9,580,230 B2
APPLICATION NO. : 14/504017
DATED : February 28, 2017
INVENTOR(S) : Tony Dai et al.

Page 1 of 1

It is certified that error appears in the above-identified patent and that said Letters Patent is hereby corrected as shown below:

On the Title Page

Item (57), ABSTRACT (Line 5): "comprise and" should be "comprise an"

In the Claims

Column 9, Line 54: "configured to operable to hold" should be "configured to hold"

Signed and Sealed this
Thirty-first Day of October, 2017

Joseph Matal
*Performing the Functions and Duties of the
Under Secretary of Commerce for Intellectual Property and
Director of the United States Patent and Trademark Office*